United States Patent
Bisselink et al.

(10) Patent No.: US 10,934,242 B2
(45) Date of Patent: Mar. 2, 2021

(54) ELECTROCHEMICAL METHOD FOR PRODUCING VALERIC ACID

(71) Applicant: Stichting Wageningen Research, Wageningen (NL)

(72) Inventors: Roel Johannes Martinus Bisselink, Kleve (DE); Marc Crockatt, s-Hertogenbosch (NL); Earl Lawrence Vincent Goetheer, Mol (BE)

(73) Assignee: Stichting Wageningen Research, Wageningen (NL)

( * ) Notice: Subject to any disclaimer, the term of this patent is extended or adjusted under 35 U.S.C. 154(b) by 0 days.

(21) Appl. No.: 16/639,534

(22) PCT Filed: Aug. 17, 2018

(86) PCT No.: PCT/NL2018/050545
§ 371 (c)(1),
(2) Date: Feb. 14, 2020

(87) PCT Pub. No.: WO2019/035715
PCT Pub. Date: Feb. 21, 2019

(65) Prior Publication Data
US 2020/0283366 A1  Sep. 10, 2020

(30) Foreign Application Priority Data

Aug. 17, 2017 (EP) .................... 17186650
Nov. 10, 2017 (EP) .................... 17201143

(51) Int. Cl.
| | |
|---|---|
| C07C 51/377 | (2006.01) |
| C07C 1/207 | (2006.01) |
| C07C 67/08 | (2006.01) |
| C25B 3/04 | (2006.01) |
| C25B 11/04 | (2021.01) |

(52) U.S. Cl.
CPC .......... *C07C 51/377* (2013.01); *C07C 1/2078* (2013.01); *C07C 67/08* (2013.01); *C25B 3/04* (2013.01); *C25B 11/0415* (2013.01)

(58) Field of Classification Search
CPC ..... C07C 1/2078; C07C 51/377; C07C 67/08; C07C 53/126; C07C 69/24; C07C 9/15; C25B 11/0415; C25B 3/04
See application file for complete search history.

(56) References Cited

PUBLICATIONS

Dos Santos et al, "Electrochemistry for the generation of renewable chemicals: electrochemical conversion of levulinic acid", RSC Advances: An International Journal to Further the Chemical Sciences, GB, vol. 5, No. 34 p. 26634-26643, Published 2015 (Year: 2015).*
International Search Report issued in PCT/NL2018/050545; dated Dec. 19, 2018.
XP055469628, Tatiane R. Dos Santos et al, "Electrochemistry for the generation of renewable chemicals: electrochemical conversion of levulinic acid", RSC Advances: An International Journal to Further the Chemical Sciences, GB, (Jan. 1, 2015), vol. 5, No. 34, doi:10.1039/C4RA16303F, ISSN 2046-2069, pp. 26634-26643, [AD] 1-15 * schemes 1, 2; paragraphs [0001], [02.2], [03.1]; figure 2 *.

* cited by examiner

*Primary Examiner* — Yevgeny Valenrod
*Assistant Examiner* — Blaine G Doletski
(74) *Attorney, Agent, or Firm* — Studebaker & Brackett PC

(57) ABSTRACT

The invention is directed to a method of electrochemically producing valeric acid.
The method of the invention comprises
  contacting a solution of levulinic acid with an anode and a cathode in an electrochemical cell; and
  electrochemically reducing levulinic acid at the cathode to form valeric acid,
wherein the cathode comprises one or more materials selected from the group consisting of cadmium, zinc, and indium.

20 Claims, 2 Drawing Sheets

ELECTROCHEMICAL METHOD FOR PRODUCING VALERIC ACID

The invention is directed to a method of electrochemically producing valeric acid.

Biomass is a particularly promising, alternative feedstock for fuels and chemicals production, given its general abundance and the potential of such processes to be more sustainable. Biomass has a complex composition. The most important classes of feedstocks derived from biomass are: carbohydrates, triglycerides, and lignocellulose. The compounds derived from these substances are termed platform chemicals. Since biogenic platform chemicals are highly oxygenated and the energy density decreases with the oxygen content in the molecule, the transformation of these molecules to low oxygenated products, via reactions as dehydrogenation, hydrogenolysis, hydrogenation, decarbonylation/decarboxylation is a fundamental step for the application of these compounds as fuels. Commonly, all target reactions involve the increase of the specific energy per mass unit in order to make the molecule more suitable as biofuel. In addition to the reduction of the oxygen content, the C—C coupling reactions are particularly interesting for biomass derived molecules and especially for these with less than 6 carbons, when the final products are to be used as fuels in diesel engines and jets. The treatment of carbohydrate based biomasses by thermal processes, including subcritical water processing, yields numerous compounds that can be directly used as biofuel or as platform chemicals. These compounds include carboxylic acids (e.g. formic acid, lactic acid, and levulinic acid), aldehydes (e.g. formaldehyde) and alcohols as well as furan and its derivatives.

Levulinic acid (4-oxopentanoic acid), which can be produced from lignocellulosic biomass, is generally considered to be an important precursor for renewable chemicals and liquid biofuels. Levulinic acid can be produced in high yields from carbohydrates and from carbohydrates and from lignocelluloses by acid catalysed hydrolysis. Its molecular structure, comprising two functional groups (a keto and a carboxyl group), makes levulinic acid an ideal platform chemical. A wide variety of value-added products can be obtained from levulinic acid by various different catalytic conversion processes. The levulinic acid derived products can in turn find application in numerous ways, for instance as building blocks for polymers, additives, resin, herbicides, pharmaceuticals, or can be applied directly as antifreeze agents, solvents, plasticisers, oxygenated fuel additives or liquid biofuels.

One of the levulinic acid derived products is valeric acid (pentanoic acid). This product finds its primary use in the synthesis of its pentanoate esters, which have pleasant odours and are used in perfumes and, cosmetics and as food additives because of their fruity flavours. Recently, Lange et al. reported the great potential of pentanoate esters as building blocks for novel oxygenated fuels, so-called 'valeric biofuels', which can be blended into both gasoline and diesel (Lange et al., Angew. Chem. Int. Ed. 2010, 49(26), 4479-4483).

Valeric acid is produced industrially (estimated 75 kton/year) via hydroformylation of 1-butene and subsequent oxidation of the formed valeraldehyde. Scheme 1 below shows the conventional industrial production of valeric acid from 1-butene (top), and other approaches based on thermocatalytic (middle) and electrochemical (bottom) conversion of levulinic acid. Bio-based levulinic acid is a building block from which valeric acid can be derived. The common approach involves hydrogenation and dehydration of levulinic acid to γ-valerolactone, followed by acid-catalysed ring-opening to 3-pentenoic acid and hydrogenation to valeric acid. This multiple step approach is typically performed at high temperatures, non-atmospheric conditions and uses catalysts based on noble metals (Lange et al., Angew. Chem. Int. Ed. 2010, 49(26), 4479-4483).

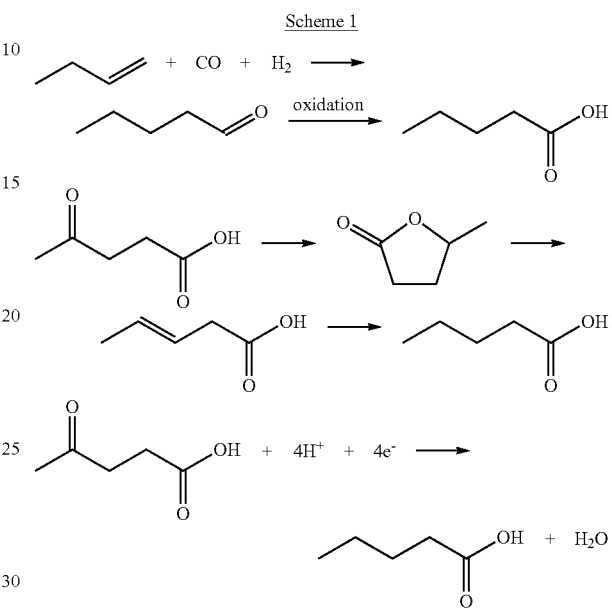

The electrochemical reduction of levulinic acid to valeric acid as shown in the bottom of scheme 1 was discovered in 1911 (Tafel et al., Z. Elektrochem. Angew. P. 1911, 17(11), 569-572) in concentrated sulphuric acid using lead and mercury as cathode material. The mechanism involves the formation of the hydroxymethyl radical, organometallic and subsequently hydrolysis to yield the hydrocarbon. Recently, these studies received renewed attention (e.g. Dos Santos et al., RCS Advances 2015, 5(34), 26634-26643). Electrochemical synthesis of valeric acid is advantageous as it is a one step approach that can be carried out in aqueous solution, at ambient pressure, at relatively low temperature, and without need for noble metals.

While it has been shown in the prior art that lead and mercury cathode materials can selectively reduce levulinic acid to valeric acid, both of these materials are toxic and harmful to the environment. Accordingly, it would be desirable to provide other less or non-toxic cathode materials that allow an efficient conversion of levulinic acid to valeric acid.

Figure 1:
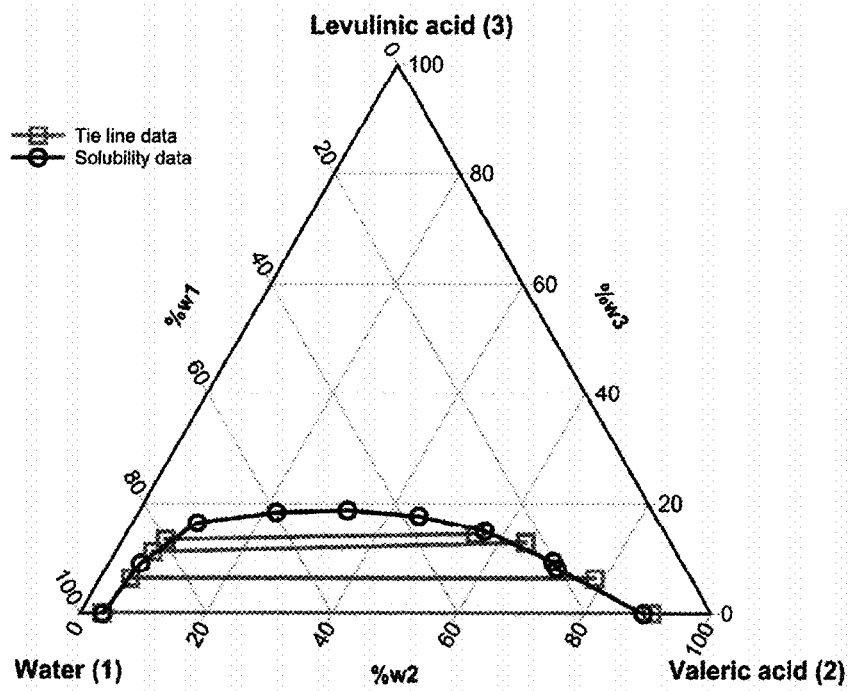
FIG. 1 shows a ternary diagram for liquid liquid extraction of the water (1)-valeric acid (2)-levulinic acid (3) system at room temperature (~20° C.).

Objective of the invention is to overcome one or more of the drawbacks faced in the prior art.

Further objective of the invention is to provide for an electrochemical method for producing valeric acid that involves limited gas evolution.

A further objective of the invention is to provide for an electrochemical method for producing valeric acid, which method has a high conversion rate.

The inventors found that one or more of these objectives can, at least in part, be met by a method in which levulinic acid is electrochemically reduced in an electrochemical cell with specific electrodes.

Accordingly, in a first aspect the invention is directed to a method for electrochemically producing valeric acid, said method comprising contacting a solution of levulinic acid with an anode and a cathode in an electrochemical cell; and electrochemically reducing levulinic acid at the cathode to form valeric acid, wherein the cathode comprises one or more materials selected from the group consisting of cadmium, zinc, and indium.

It was surprisingly found by the inventors that by choosing specific electrode materials it was possible to provide an electrochemical method of producing valeric acid from levulinic acid with minimal gas evolution and desirable current efficiencies for the production of valeric acid. Additionally, the method of the invention is highly selective towards the production of valeric acid.

The method of the invention can suitable be carried out in an electrochemical cell comprising an anode in an anode electrolyte solution, and a cathode in a cathode electrolyte solution, wherein the cathode is in electrical communication with the anode. The method of the invention may be performed in a divided electrochemical cell (i.e. an electrochemical cell wherein the anolyte and the catholyte are divided by a membrane), or an undivided cell (i.e. an electrochemical cell wherein the anolyte and catholyte are undivided and consequently the same electrolyte).

To operate the method, a voltage source is used to apply a cathode potential to the cathode and a potential difference is created between the cathode and the anode. Driven by this potential difference, electrons flow from the anode to the cathode through an external wire. The electrons at or near the cathode undergo reduction reactions with species contained in the cathode electrolyte solutions, while oxidation reactions occur at or near the anode. In accordance with the invention levulinic acid is reduced at or near the cathode.

Preferably, the applied cathode potential is in the range of $-2.0$ to $-1.2$ V vs. SCE (saturated calomel electrode), such as $-1.9$ to $-1.3$ V vs. SCE. The applied current may vary and can, for example, be in the range of 50-500 mA/cm$^2$, such as 100-350 mA/cm$^2$, or 120-250 mA/cm$^2$.

The cathode used in the method of the invention can comprise one or more materials selected from the group consisting of cadmium, indium and zinc. More preferably, the cathode of the invention comprises one or more materials selected from the group consisting of indium and zinc, even more preferably the cathode of the invention comprises indium. In an embodiment, the cathode is present in the form of a wire. The inventors found that in particular indium and zinc exhibit high selectivity towards valeric acid. In addition, reduction of levulinic acid occurs at a high potential at indium and zinc, which is beneficial in terms of energy usage. Compared to lead, cathodic dissolution due to formation of intermediate organometallics is favourably limited when using cadmium.

The method of the invention allows a conversion of levulinic acid of 50% or more, such as 60% or more, 70% or more, 80% or more, 90% or more, or 95% or more. Advantageously, the method of the invention is highly selective in converting levulinic acid into valeric acid and the amount of γ-valerolactone produced as by-product is relatively low. Suitably, the method of the invention has a selectivity towards valeric acid of 80% or more, such as 85% or more, or 95% or more. Suitably, the method of the invention has a selectivity towards γ-valerolactone of 10% or less, such as 7% or less, or 5% or less. Conversion is defined as the fraction of reactant being converted in the process. Selectivity is defined as the fraction of a product in the total converted product.

The anode used in the method of the invention can comprise one or more materials selected from the group consisting of graphite, boron doped diamond, vitreous carbon, platinum, iridium, ruthenium, tantalum, hafnium, or niobium, and noble metal-coated titanium, tantalum, hafnium, or niobium, such as platinum, platinum oxide, rhodium, rhodium oxide, tantalum, tantalum oxide, iridium, iridium oxide, ruthenium, and ruthenium oxide. In a preferred embodiment, the anode material comprises one or more selected from the group consisting of iridium oxide, platinum oxide, ruthenium oxide, tantalum oxide, and titanium. This material may be present on the anode in the form of a layer, such as a sputtered layer. Also mixed metal oxides (MMO), that typically consist of platinum, iridium and/or ruthenium on titanium, with tantalum as an intermediate layer can be used as suitable materials for the anode.

In case a divided electrochemical cell (typically a two-compartment electrochemical cell) is used, the anolyte solution and catholyte solution are divided by a membrane. The catholyte solution in that case comprises levulinic acid. The membrane can be a semi-permeable membrane, a diaphragm or a porous pot. Some examples of commercially available membranes include Nafion™ HP, Nafion™ 211, Nafion™ XL, Nafion™ 212, Nafion™ NE1035, Nafion™ 115, Nafion™ 117, Nafion™ 1110, Nafion™ N324, Nafion™ N424, Nafion™ N438, Fumatech FAS, Fumatech FKS, Fumatech FAB, Fumatech FKB, Fumatech FBM, Fumatech FAD, Fumatech FKD, Fumatech FAP, Fumatech FAA, Fumatech FKL, Fumatech FKE, Neosepta™ CMX, Neosepta™ CMS, Neosepta™ CMB, Neosepta™ AMX, Neosepta™ AHA, Neosepta™ ACS, Neosepta™ AFN, Neosepta™ AFX, Neosepta™ ACM, Selemion™ CMV, Selemion™ CMD, Selemion™ AMV, Selemion™ AMT, Selemion™ DSV, Selemion™ HSF, Selemion™ CSD, Selemion™ CMF, Selemion™ AAV, Selemion™ ASV, Selemion™ AHO, and Selemion™ APS4.

The catholyte solution can be aqueous and/or non-aqueous. Preferably, the catholyte solution is aqueous. Apart from the levulinic acid, the catholyte solution may comprise one or more selected from the group consisting of a buffer, sodium perchlorate, sodium sulphate, sodium chloride, sodium bromide, sodium hydroxide, sodium carbonate, sulphuric acid, hydrochloric acid, nitric acid, perchloric acid, alkylsulphonic acid, acetic acid, potassium sulphate, potassium chloride, potassium perchlorate, potassium bromide, potassium hydroxide, potassium carbonate, ammonium sulphate, ammonium chloride, ammonium perchlorate, ammonium bromide, ammonium hydroxide, ammonium carbonate. Preferably, the catholyte solution comprises one or more selected from the group consisting of sulphuric acid, sodium sulphate, perchloric acid, and alkylsulphonic acid.

The anolyte solution can be aqueous or non-aqueous. Preferably, the anolyte solution is aqueous. The anolyte solution may comprise one or more selected from the group consisting of a buffer, sodium perchlorate, sodium sulphate, sodium chloride, sodium bromide, sodium hydroxide, sodium carbonate, sulphuric acid, hydrochloric acid, nitric acid, perchloric acid, alkylsulphonic acid, acetic acid, potassium sulphate, potassium chloride, potassium perchlorate, potassium bromide, potassium hydroxide, potassium carbonate, ammonium sulphate, ammonium chloride, ammonium perchlorate, ammonium bromide, ammonium hydroxide, and ammonium carbonate. Preferably, the anolyte solution comprises one or more selected from the group consisting of sulphuric acid, sodium sulphate, perchloric acid, and alkylsulphonic acid.

In case an undivided electrochemical cell is used, the anolyte solution and catholyte solution are the same and at least comprise levulinic acid. In such case, the solution can further comprise one or more selected from the group consisting of a buffer, sodium perchlorate, sodium sulphate, sodium chloride, sodium bromide, sodium hydroxide, sodium carbonate, sulphuric acid, hydrochloric acid, nitric acid, perchloric acid, alkylsulphonic acid, acetic acid, potassium sulphate, potassium chloride, potassium perchlorate, potassium bromide, potassium hydroxide, potassium carbonate, ammonium sulphate, ammonium chloride, ammonium perchlorate, ammonium bromide, ammonium hydroxide, ammonium carbonate. Preferably, the solution comprises one or more selected from the group consisting of sulphuric acid, sodium sulphate, perchloric acid, and alkylsulphonic acid.

In case an undivided electrochemical cell is used, the anolyte solution and the catholyte solution are the same.

The anolyte solution and/or the catholyte solution preferably comprises a polar solvent, such as water, methanol, short chain alcohols or a mixture thereof. Preferably, the anolyte solution and/or catholyte solution at least comprise water as solvent.

Preferably, the concentration of levulinic acid is 0.05 M or more, more preferably 0.1 M or more, and even more preferably 0.3 M or more, such as a concentration of up to 5 M, up to 3 M or up to 1 M. Upon performing the method of the invention and electrochemically reducing levulinic acid, typically a two-phase system is achieved. The concentration of levulinic acid can be used to tune the composition of both phases so as to optimise them for further processing steps, such as separation and collection. This is illustrated by the ternary diagram shown in FIG. 1 for liquid-liquid extraction of the water (1)-valeric acid (2)-levulinic acid (3) system at room temperature (~20° C.).

The method of the invention can suitably be carried out at ambient (or slightly elevated) temperatures and pressures. The method can thus suitably be carried out at a temperature of at a temperature of 20° C. or more, 30° C. or more, or 40° C. or more. The method of the invention can suitably be carried out at a temperature of 80° C. or less, such as 70° C. or less, or 60° C. or less. The invention may be carried out at a pressure of 51-152 kPa (0.5-1.5 atm), preferably 81-122 kPa (0.8-1.2 atm), such as 91-111 kPa (0.9-1.1 atm).

It is preferred that during the method of the invention, the pH is kept at a value of 2 or less, such as 1 or less, or 0 or less. Preferably, the pH is kept at a value of −1.2 or more, such as −1.0 or more, −0.7 or more, or −0.4 or more. The pH can, for instance, be in the range of −1.2 to 2.0, preferably −1.0 to 1.5, more preferably −0.7 to 1.2, even more preferably −0.3 to 1.0.

Advantageously, the method of the invention results in the formation of a two phase system, wherein one phase is rich in valeric acid while the other phase is rich in water. The levulinic acid will be divided over the two phases as a function of the conversion, as shown in the ternary diagram in FIG. 1. Hence, the solution comprising valeric acid phase separates during the operation of the method of the invention. This allows to suitably separate the valeric acid product from the levulinic acid starting material by phase separation. This spontaneous separation of valeric acid shows a clear advantage of the method of the invention over conventional techniques. Accordingly, the method of the invention can suitably further comprise phase separating a valeric acid rich phase from a levulinic acid rich phase and collecting valeric acid. The valeric acid can then be collected and optionally purified.

Purification of the collected valeric acid rich phase may involve methods such as distillation and/or extraction.

The method of the invention may be performed both in batch or continuous. When performing the method of the invention in continuous manner, an electrochemical continuous flow cell can be used.

For the manufacture of valuable biofuels, the valeric acid produced by the method of the invention may be further subjected to esterification so as to produce different valerates. Accordingly, the method of the invention suitably further comprises esterifying at least part of the valeric acid to produce valerates, in particular alkyl valerates, such as methyl valerate, ethyl valerate, propyl valerate, butyl valerate, and pentyl valerate. From a chemical kinetic point of view, such alkyl valerates behave similarly to alkanes, with a potentially cool flame, a negative temperature coefficient, and high-temperature reactivity, depending on the length of the carbon chain.

Optionally, the method of the invention may further comprise conversion of valeric acid at the anode to octane, typically n-octane. The produced n-octane may, e.g., be used as solvent, cleaning agent, fuel additive or as reaction agent.

The invention has been described by reference to various embodiments, and methods. The skilled person understands that features of various embodiments and methods can be combined with each other.

All references cited herein are hereby completely incorporated by reference to the same extent as if each reference were individually and specifically indicated to be incorporated by reference and were set forth in its entirety herein.

The use of the terms "a" and "an" and "the" and similar referents in the context of describing the invention (especially in the context of the claims) are to be construed to cover both the singular and the plural, unless otherwise indicated herein or clearly contradicted by context. The terms "comprising", "having", "including" and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. For the purpose of the description and of the appended claims, except where otherwise indicated, all numbers expressing amounts, quantities, percentages, and so forth, are to be understood as being modified in all instances by the term "about". Also, all ranges include any combination of the maximum and minimum points disclosed and include any intermediate ranges therein, which may or may not be specifically enumerated herein.

Preferred embodiments of this invention are described herein. Variation of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject-matter recited in the claims appended hereto as permitted by applicable law. Moreover, any combination of the above-described elements in all possible variations thereof is encompassed by the invention unless otherwise indicated herein or otherwise clearly contradicted by context. The claims are to be construed to include alternative embodiments to the extent permitted by the prior art.

For the purpose of clarity and a concise description features are described herein as part of the same or separate embodiments, however, it will be appreciated that the scope of the invention may include embodiments having combinations of all or some of the features described.

The invention will now be further illustrated by means of the following examples, which are not intended to limit the scope in any manner.

EXAMPLES

Various materials were selected based on their high overpotential for the hydrogen evolution reaction. The applicability was assessed by preparative electrolysis (H-cell) performed at constant current (150 mA/cm$^2$) and at a temperature of 50° C. Analysis was performed by high performance liquid chromatography (HPLC), $^1$H-NMR and inductively coupled plasma mass spectrometry (ICP-MS). The H-cell was a two-compartment cell containing 150 ml of catholyte (1 M H$_2$SO$_4$ and 0.5 M levulinic acid), and 150 ml of anolyte (1 M H$_2$SO$_4$), separated by a Nafion™ 117 membrane. The H-cell contained a wire cathode of 70 cm length and an iridium oxide anode. All solutions were removed from the cell, and the cell was rinsed with demineralised water. All solutions were collected, put together and analysed.

The electrolysis results for various cathode materials are shown in Table 1 below. In table 1, charge denotes the relevant charge added to levulinic acid, $E_{av}$ is average potential of the reference electrode, $X_{LA}$ is conversion of levulinic acid, $S_{VA}$ is the selectivity towards valeric acid, $S_{gVL}$ is the selectivity towards γ-valerolactone, $CE_{VA}$ is the current efficiency, and M is the concentration of metal in solution at the end of electrolysis. The indicated selectivity values are based on HPLC analysis.

TABLE 1

Electrolysis results for different cathode materials

| Ex. | cathode material | charge [F/mol] | $E_{av}$ [V vs. SCE] | $X_{LA}$ [%] | $S_{VA}$ [%] | $S_{gVL}$ [%] | $CE_{VA}$ [%] | M [mg/l] |
|---|---|---|---|---|---|---|---|---|
| 1 | Pb | 8.2 | −1.77 | 99 | 92 | 2.2 | 47 | 27.8 (9.2) $^d$ |
| 2 | Cd | 8.3 | −1.77 | 98 | 89 | 3.8 | 45 | 18.7 |
| 3 | In | 8.3 | −1.58 | 90 | 99 | 0 | 45 | 107 |
| 4 | Zn | 8.3 | −1.41 | 56 | 95 | 1.7 | 27 | 61.1 |
| 5 | Al | 8.3 | −2.11 | 14 | 71 | 22 | 5.6 | 1924 |
| 6 | Ni | 8.2 | −0.96 | 7.3 | 74 | 21 | 2.7 | 6.5 |
| 7 | Ga $^a$ | 8.2 | −1.97 $^c$ | 0 | 0 | 0 | 0 | 96.0 |
| 8 | Ag | 8.2 | −1.12 | 0 | 0 | 0 | 0 | 0.12 |
| 9 | Ti $^b$ | 3.9 | −1.32 | 0 | 0 | 0 | 0 | 0.12 |
| 10 | Sn | 8.2 | −1.22 | 0 | 0 | 0 | 0 | 2.1 $^e$ |

Figure 2:
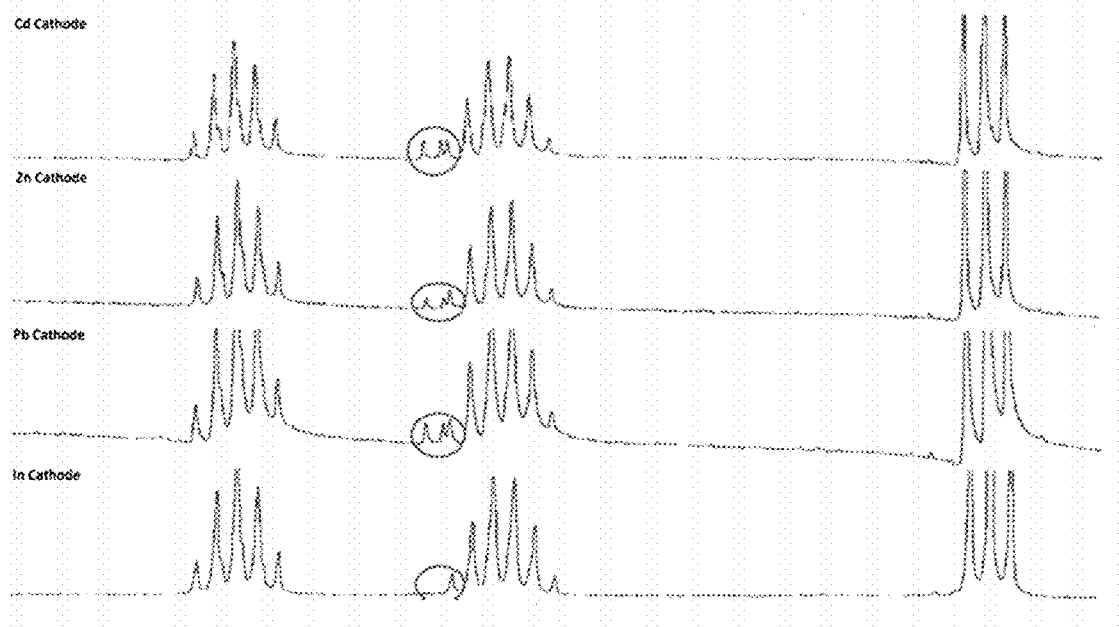
FIG. 2 shows conversion of levulinic acid and selectivity towards valeric acid being confirmed by 1H NMR analysis. In the figure, a 1H NMR overlay (0.7 1.6 ppm) shows impurity (red circle) in samples obtained at lead, cadmium, zinc cathodes and not at the indium cathode.
Figure 3:
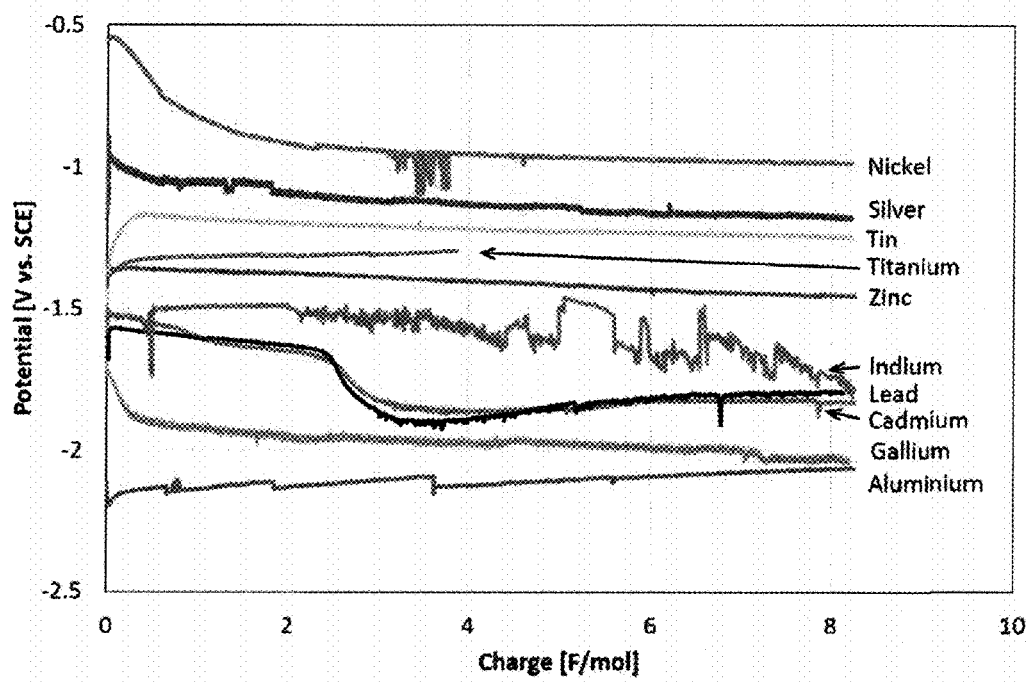
FIG. 3 shows the electrode potential of various cathode materials during electrolysis of 0.5 M levulinic acid in 1 M $H_2SO_4$ at 50° C.

$^a$ a gallium pool electrode (15.9 cm$^2$)
$^b$ 22 cm wire
$^c$ corrected for iR drop
$^d$ total Pb concentration, between brackets Pb as precipitate
$^e$ some precipitates noticed in solution and not taken into account Table 1 clearly shows that next to lead and mercury, also indium, cadmium and zinc are able to reduce levulinic acid to valeric acid with high selectivity. Other materials with a high overpotential for the hydrogen evolution reaction (Al, Ga, Ti and Sn) are however, not able to reduce levulinic acid. The obtained valeric acid and γ-valerolactone (as identified by HPLC) selectivity for lead is similar to reported in literature (Nilges et al., *Energy & Environmental Science* 2012, 5(1), 5231-5233; Xin et al., *ChemSusChem* 2013, 6(4), 674-686; Qiu et al., *Green Chemistry* 2014, 16(3), 1305-1315; Dos Santos et al., *RCS Advances* 2015, 5(34), 26634-26643; each based on HPLC analysis). Conversion of levulinic acid and selectivity towards valeric acid is confirmed by $^1$H-NMR analysis, as shown in FIG. 2 (a $^1$H-NMR overlay (0.7-1.6 ppm) showing impurity (red circle) in samples obtained at lead, cadmium, zinc cathodes and not at the indium cathode). Indium and zinc exhibit the highest selectivity towards valeric acid. In addition, reduction of levulinic acid occurs at a higher potential at indium and zinc. This is shown in FIG. 3, which displays the electrode potential of various cathode materials during electrolysis of 0.5 M levulinic acid in 1 M H$_2$SO$_4$ at 50° C.

In an additional experiment, the formation of a two-phase system is shown (FIG. 4) for zinc, cadmium and lead cathode materials. This figure shows the concentration of levulinic acid versus the supplied charge. Initially, the concentration of levulinic acid follows Faradays law (four electron reduction to valeric acid) to approximately 25% conversion, i.e. a concentration of about 0.25 mol/l valeric acid at about 100% selectivity. After this point, a two phase system develops resulting in an additional decrease of levulinic acid due to its dissolution in the valeric acid phase.

Figure 4:
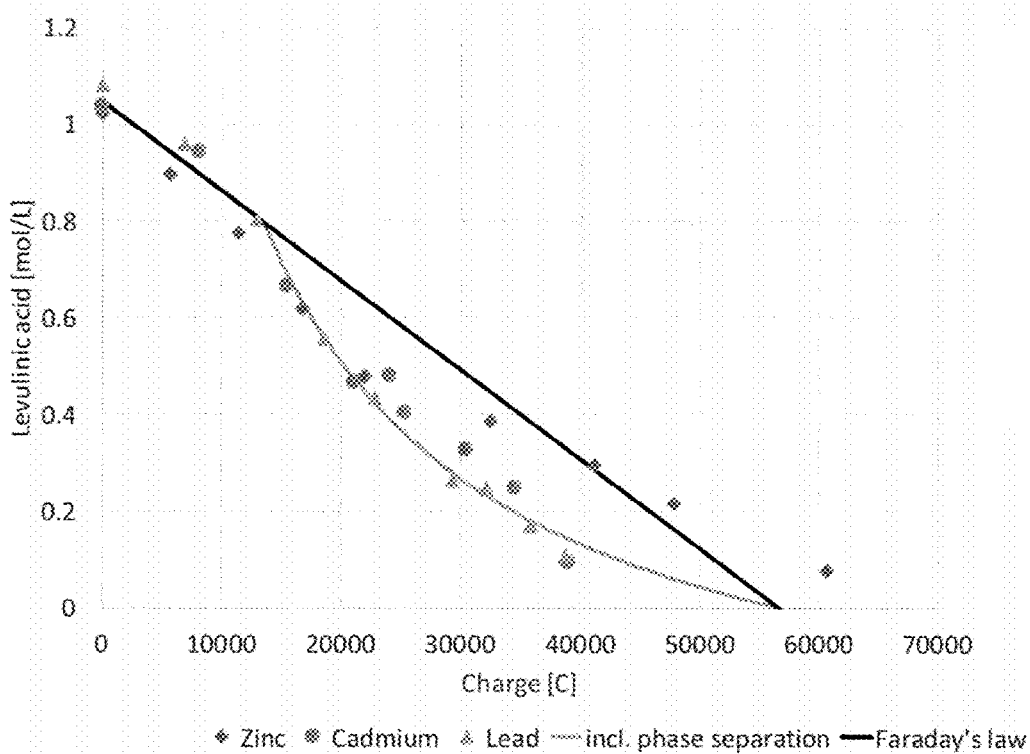
FIG. 4 shows the formation of a two phase system for zinc, cadmium and lead cathode materials. This figure shows the concentration of levulinic acid versus the supplied charge.

The point of formation of the second phase is somewhat lower than the solubility of valeric acid, viz. 0.39 M at 50° C. (Romero et al., *J. Solution Chem.* 2009, 38(3), 315-320). This might be explained by: i) the salting out effect due to the presence of 1 M of sulphuric acid, and/or ii) the presence of an additional solute, levulinic acid. The solid black line in FIG. 4 depicts the theoretical decrease of levulinic acid based on the supplied amount of electrons to the system (Faraday's law). The grey line depicts the effect of the formation of a second phase on the concentration dependency, taking into account a solubility of 0.25 mol/l valeric acid and a distribution coefficient of 25 for levulinic acid.

The invention claimed is:

1. A method for electrochemically producing valeric acid, said method comprising
    contacting a solution of levulinic acid with an anode and a cathode in an electrochemical cell; and
    electrochemically reducing levulinic acid at the cathode to form valeric acid, wherein the cathode comprises one or more materials selected from the group consisting of cadmium, zinc, and indium.

2. The method according to claim 1, wherein the cathode comprises indium.

3. The method according to claim 1, wherein the anode comprises one or more materials selected for the group consisting of iridium oxide, platinum oxide, ruthenium oxide, tantalum oxide, and titanium.

4. The method according to claim 1, wherein said electrochemical cell is an undivided electrochemical cell.

5. The method according to claim 1, wherein said electrochemical cell is a divided electrochemical cell.

6. The method according to claim 1, wherein said method has a conversion of levulinic acid of 50% or more.

7. The method according to claim 1, wherein said method has
    i) a selectivity towards valeric acid of 80% or more; and/or
    ii) a selectivity towards γ-valerolactone of 10% or less.

8. The method according to claim 1, wherein the aqueous solution of levulinic acid further comprises one or more selected from the group consisting of sulphuric acid, sodium sulphate, perchloric acid, and alkylsulphonic acid.

9. The method according to claim 1, which method is carried out at a temperature of 20-80° C.

10. The method according to claim 1, wherein the pH of the aqueous solution is kept within the range of −1.2 to 2.0.

11. The method according to claim 1, wherein a current is imposed on the electrochemical cell, said current having a current density of 50-500 mA/cm$^2$.

12. The method according to claim 1, wherein said aqueous solution further comprises a strong acid.

13. The method according to claim 1, wherein said method further comprises phase separating a valeric acid rich phase from a levulinic acid rich phase.

14. The method according to claim 1, further comprising esterifying the valeric acid to produce valerates.

15. The method according to claim 1, said method further comprising converting valeric acid into octane at an anode of the electrochemical cell.

16. The method according to claim 1, wherein said aqueous solution further comprises one or more selected from the group consisting of sulphuric acid and alkylsulphonic acid.

17. The method according to claim 1, further comprising esterifying the valeric acid to produce one or more valerates selected from the group consisting of methyl valerate and ethyl valerate.

18. The method according to claim 1, further comprising esterifying the valeric acid to produce propyl valerate.

19. The method according to claim 1, further comprising esterifying the valeric acid to produce butyl valerate.

20. The method according to claim 1, further comprising esterifying the valeric acid to produce pentyl valerate.

* * * * *